United States Patent
Zhiyu et al.

(10) Patent No.: US 11,751,854 B2
(45) Date of Patent: Sep. 12, 2023

(54) LIQUID-COLLECTING MECHANISM WITH ARRAYED MESH COLLECTION AREA AND SMART TOILET CONTAINING SAME

(71) Applicant: Shanghai Kohler Electronics, Ltd., Shanghai (CN)

(72) Inventors: Qin Zhiyu, Beijing (CN); Qintao Sun, Beijing (CN); Ping Yuan, Beijing (CN)

(73) Assignee: Shanghai Kohler Electronics, Ltd., Shanghai (CN)

( * ) Notice: Subject to any disclaimer, the term of this patent is extended or adjusted under 35 U.S.C. 154(b) by 957 days.

(21) Appl. No.: 16/245,760

(22) Filed: Jan. 11, 2019

(65) Prior Publication Data

US 2019/0216442 A1 Jul. 18, 2019
US 2021/0059647 A9 Mar. 4, 2021

(30) Foreign Application Priority Data

Jan. 12, 2018 (CN) .......................... 201810032512.4

(51) Int. Cl.
*A61B 10/00* (2006.01)
*E03D 9/00* (2006.01)

(52) U.S. Cl.
CPC .............. *A61B 10/007* (2013.01); *E03D 9/00* (2013.01)

(58) Field of Classification Search
CPC ........... E03D 9/002; E03D 9/00; E03D 9/005; E03D 9/007; E03D 2009/028; E03D 9/02; E03D 11/13; A47K 11/10; A61B 10/007
See application file for complete search history.

(56) References Cited

U.S. PATENT DOCUMENTS

| | | | |
|---|---|---|---|
| 2,958,222 | A | 11/1960 | Willard |
| 3,315,530 | A | 4/1967 | Woodley, Jr. |
| 3,466,145 | A | 9/1969 | Van Duyne |

(Continued)

FOREIGN PATENT DOCUMENTS

| | | |
|---|---|---|
| CN | 2745070 Y | 12/2005 |
| CN | 201222065 Y | 4/2009 |

(Continued)

OTHER PUBLICATIONS

KR Office Action on KR Patent Application Ser. No. 10-2019-0002173 dated Oct. 15, 2020 (6 pages).

(Continued)

*Primary Examiner* — David J. McCrosky
(74) *Attorney, Agent, or Firm* — LEMPIA SUMMERFIELD KATZ LLC

(57) ABSTRACT

A liquid collecting mechanism that includes a liquid collection tube arm and a liquid collection tube head fixed at a front end of the tube arm. A sealing spacer is arranged at a joint connecting the liquid collection tube head and the liquid collection tube arm, and the liquid collection tube head is internally provided with a liquid collection cavity. An area of the liquid collection tube head located above the liquid collection cavity is a mesh collection area, and a plurality of collecting holes is provided in the mesh collection area. The mechanism includes a liquid suction tube passing through the tube arm and tube head, and the liquid suction tube has an open first end located in the liquid collection cavity and an open second end configured to connect with a pump body mechanism.

20 Claims, 2 Drawing Sheets

(56) References Cited

U.S. PATENT DOCUMENTS

| | | | |
|---|---|---|---|
| 3,625,064 A | 12/1971 | Hinman, Jr. | |
| 3,625,654 A | 12/1971 | Van | |
| 3,659,461 A | 5/1972 | Thompson | |
| 3,707,869 A | 1/1973 | Raynor | |
| 3,735,641 A | 5/1973 | Bink | |
| 3,802,270 A | 4/1974 | Daniels | |
| 3,832,904 A | 9/1974 | Dreuw | |
| 4,165,645 A | 8/1979 | Cooper | |
| 4,203,169 A | 5/1980 | Dale | |
| 4,252,132 A | 2/1981 | Kuntz | |
| 4,276,889 A | 7/1981 | Kuntz et al. | |
| 4,331,162 A | 5/1982 | Kuntz et al. | |
| 4,338,842 A | 7/1982 | Collins | |
| 4,631,968 A | 12/1986 | Aske | |
| 4,636,474 A | 1/1987 | Ogura et al. | |
| 4,743,155 A | 5/1988 | Carey et al. | |
| 4,771,642 A | 9/1988 | Parth et al. | |
| 4,962,550 A | 10/1990 | Ikenaga et al. | |
| 5,062,304 A | 11/1991 | Van Buskirk et al. | |
| 5,111,539 A | 5/1992 | Hiruta et al. | |
| 5,121,641 A | 6/1992 | Silver | |
| 5,563,384 A | 10/1996 | Marlow et al. | |
| 5,625,911 A | 5/1997 | Nakayama et al. | |
| 5,720,054 A | 2/1998 | Nakayama et al. | |
| 5,730,149 A * | 3/1998 | Nakayama | G01N 1/12 600/573 |
| 5,844,148 A | 12/1998 | Klein et al. | |
| 6,772,450 B1 * | 8/2004 | Saylor | E03D 9/005 4/223 |
| 6,843,103 B2 | 1/2005 | Aguilera et al. | |
| 6,951,545 B2 | 10/2005 | Smith et al. | |
| 7,100,424 B2 | 9/2006 | Wilson | |
| 8,312,780 B2 | 11/2012 | Blacklin et al. | |
| 8,935,965 B1 | 1/2015 | Selbig et al. | |
| 9,176,026 B2 | 11/2015 | Sidorsky et al. | |
| 10,383,606 B1 | 8/2019 | Mccord | |
| 2010/0058777 A1 | 3/2010 | Walter | |
| 2011/0113899 A1 | 5/2011 | Dahler et al. | |
| 2015/0359522 A1 * | 12/2015 | Recht | G01N 21/255 600/573 |
| 2016/0287155 A1 * | 10/2016 | Kelly | A61B 10/007 |
| 2017/0114531 A1 * | 4/2017 | Ye | A61B 10/007 |
| 2018/0372717 A1 | 12/2018 | Tu et al. | |
| 2019/0170728 A1 | 6/2019 | Qin | |
| 2020/0271578 A1 | 8/2020 | Yamasaki | |
| 2020/0309646 A1 | 10/2020 | Qin et al. | |

FOREIGN PATENT DOCUMENTS

| | | | |
|---|---|---|---|
| CN | 101551306 B | 1/2011 | |
| CN | 201731946 U | 2/2011 | |
| CN | 102802526 A | 11/2012 | |
| CN | 204685875 U | 10/2015 | |
| CN | 205157255 U | 4/2016 | |
| CN | 105842013 A * | 8/2016 | G01F 23/263 |
| CN | 205607700 U | 9/2016 | |
| CN | 206132738 U | 4/2017 | |
| CN | 108713990 A * | 10/2018 | |
| CN | 112649239 A | 4/2021 | |
| CN | 111719653 B | 5/2021 | |
| DE | 20314472.0 U1 | 11/2003 | |
| GB | 2 123 951 A | 2/1984 | |
| JP | S51-101982 U | 8/1976 | |
| JP | S5110982 | 8/1976 | |
| JP | H584863 | 11/1993 | |
| JP | H07-234217 | 9/1995 | |
| JP | 19-95234216 | 3/1997 | |
| JP | 2000-258411 A | 9/2000 | |
| JP | 2004-092385 | 3/2004 | |
| JP | 2008-537775 A | 9/2008 | |
| JP | 2010-066263 A | 3/2010 | |
| JP | 6478128 B2 | 3/2019 | |
| KR | 101080828 | 11/2011 | |
| TW | 515719 | 1/2003 | |
| WO | WO-2006/101833 | 9/2006 | |
| WO | WO-2017/185690 | 11/2017 | |
| WO | WO-2020/078018 A1 | 4/2020 | |
| WO | WO-2020/099977 A1 | 5/2020 | |

OTHER PUBLICATIONS

International Preliminary Report on Patentability for PCT Appl. Ser. No. PCT/CN2016/103219 dated Nov. 8, 2018 (14 pages).

International Search Report and Written for PCT Appl. Ser. No. PCT/CN2016/103219 dated Feb. 6, 2017 (19 pages).

Japanese Office Action for JP Appl. Ser. No. 2019-506770 dated Jun. 26, 2020 (3 pages).

Japanese Office Action for JP Appl. Ser. No. 2019-506770 dated Oct. 8, 2019 (13 pages).

Korean Office Action for KR Appl. Ser. No. 10-2018-7034095 dated Jul. 14, 2020 (9 pages).

Non-Final Office Action on U.S. Appl. No. 16/245,760 dated Aug. 27, 2021 (22 pages).

Taiwanese Office Action for TW Appl. Ser. No. 108100243 dated May 20, 2019 (6 pages).

U.S. Office Action on U.S. Appl. No. 16/097,172 dated Nov. 2, 2021.

Japanese Office Action on JP Appl. No. 2018-239443 dated Nov. 26, 2019 (4 pages).

Japanese Office Action on JP Appl. No. 2020-069588 dated Mar. 16, 2021 (3 pages).

* cited by examiner

LIQUID-COLLECTING MECHANISM WITH ARRAYED MESH COLLECTION AREA AND SMART TOILET CONTAINING SAME

CROSS-REFERENCE TO RELATED APPLICATIONS

The present application claims the benefit of and priority to Chinese Patent Application No. 20181032512.4, which was filed on Jan. 12, 2018, and is incorporated by reference herein in its entirety.

TECHNICAL FIELD

The present disclosure relates to the field of urine detection technologies, and more particularly, to a liquid-collecting mechanism with an arrayed mesh collection area and a smart toilet containing the same.

BACKGROUND

Currently, most urine detections are performed in hospital after the examinees manually collect urine thereof. Finishing the urine detection in hospital not only requires registration in hospital for treatment, but also has hygienic problems. Some of the present smart toilets perform urine detection by collecting urine in an inside surface of the toilet, which causes the cross-contamination problem of the urine sample, so that the detection result is inaccurate. Further, according to Chinese Patent Application No. 201610279185.3), titled A LIQUID-COLLECTION DEVICE AND A SMART TOILET CONTAINING THE SAME, the liquid-collection device can flexibly collect the urine in the air, which is simple and convenient, and also avoids cross contamination. However, a suction tube assembly in the liquid-collection device needs to move continuously under the drive of a driving mechanism to search for urine, so as to collect dispersed urine. And the urine in the cavity of the suction tube assembly is not easy to be completely emptied, which easily leads to unclean flushing and affects the accuracy of the result.

Thus, it can be seen that the existing liquid-collection devices and methods are inconvenient and have defects, and need to be further improved. How to create a liquid-collecting mechanism with an arrayed mesh collection area and a smart toilet containing the liquid-collecting mechanism so as to have simple structure, accurate result and low cost is one of the important research and development topics currently underway.

SUMMARY

A technical problem to be solved by the present disclosure is to provide a liquid-collecting mechanism, which can realize liquid-collection in air with low cost and in a simple and reliable manner, so as to overcome the defects of the existing liquid-collecting mechanism device.

In order to solve the technical problem above, the present disclosure provides a liquid-collecting mechanism, which includes:

a liquid-collection tube arm;

a liquid-collection tube head fixed at a front end of the liquid-collection tube arm, wherein a sealing spacer is arranged at a joint of the liquid-collection tube head and the liquid-collection tube arm, the liquid-collection tube head is internally provided with a liquid-collection cavity, an area of the liquid-collection tube head located above the liquid-collection cavity is a mesh collection area, and the mesh collection area is provided with a plurality of collecting holes; and a liquid-suction tube, wherein an opening at one end of the liquid-suction tube is located in the liquid-collection cavity, an opening at the other end of the liquid-suction tube passes through the sealing spacer and the liquid-collection tube arm, and is used for being connected with a pump body mechanism.

As an improvement of the present disclosure, the plurality of collecting holes in the mesh collection area are arranged in an array arrangement mode.

Another improvement, the liquid-collection tube head is provided with an air discharge hole or an air discharge groove communicated with the liquid-collection cavity.

Another improvement, the liquid-collecting mechanism can include a liquid-discharge tube, an opening at one end of the liquid-discharge tube is located in the liquid-collection cavity, and an opening at the other end of the liquid-discharge tube passes through the sealing spacer and the liquid-collection tube arm, and is used for being connected with the pump body mechanism.

Another improvement, a portion of the tube wall of the liquid-discharge tube located in the liquid-collection cavity can be further provided with an auxiliary liquid-discharge hole.

Another improvement, a plurality of auxiliary liquid-discharge holes can be arranged in an array along an axial direction of the liquid-discharge tube.

Another improvement, the liquid-suction tube and the liquid-discharge tube can be fixedly connected side by side.

Another improvement, a portion of the liquid-discharge tube in the liquid-collection cavity can be integrally formed with the liquid-collection tube head.

Another improvement, a portion of the liquid-suction tube in the liquid-collection cavity can be integrally formed with the liquid-collection tube head.

Another improvement, the liquid-collection tube head, the liquid-collection tube arm and the sealing spacer can be integrally formed.

Another improvement, at least one of the liquid-collection tube head and the liquid-collection tube arm can be integrally formed with the sealing spacer.

Another improvement, the liquid-collecting mechanism can include a liquid level sensing unit used for monitoring a liquid volume collected in the liquid-collection cavity in real time.

Another improvement, the liquid level sensing unit can include a steel needle, a control circuit board and a wire, one end of the steel needle is arranged in the liquid-collection cavity, its end face is located at an upper portion of the liquid-collection cavity and does not exceed a vertical plane of the collecting hole closest to the liquid-collection tube arm end, and the other end of the steel needle is connected with the control circuit board through the wire.

The present disclosure further provides a smart toilet, the smart toilet includes the liquid-collecting mechanism above, and when the liquid-collecting mechanism collects urine, the urine is received by the plurality of collecting holes in the mesh collection area.

After using the design, the present invention at least has the following advantages.

According to the present invention, the area for collecting the urine is increased through the arrangement of the array mesh collection area, the method for moving a position of the urine-suction hole by using a driving mechanism in the prior art is replaced, so that the cost is reduced, and meanwhile, blockage caused by foreign impurities entering into the liquid-collection tube may be prevented, and the problem of splashing urine may be avoided.

According to the present invention, a plurality of liquid-discharge holes is arranged at different positions in the liquid-discharge tube, so that a speed of discharging cleaning liquid may be greatly increased, and the cleaning liquid at each position in the liquid-collection cavity can be discharged out.

According to the present invention, the air discharge hole or the air discharge groove is arranged to prevent the liquid-collection cavity from forming an air trapping area while collecting liquid, so as to solve the problem that the liquid-collection cavity cannot be fully filled with the urine.

The liquid-collecting mechanism of the present disclosure is simple in structure, safe and reliable, and low in manufacturing cost, and the liquid-collecting mechanism has faster liquid discharge speed and higher evacuation rate.

BRIEF DESCRIPTION OF THE DRAWINGS

The foregoing description is merely a summary of the technical solutions of the present invention. To understand the technical means of the present invention more clearly, the present invention is further described in detail with reference to the figures and the detailed embodiments hereinafter.

DETAILED DESCRIPTION

Taking the liquid-collecting mechanism used as a urine-collecting device of a smart toilet as an example, the embodiment describes the liquid-collecting mechanism in detail, which shall not be construed as any limitation on the liquid-collecting mechanism.

Figure 1:
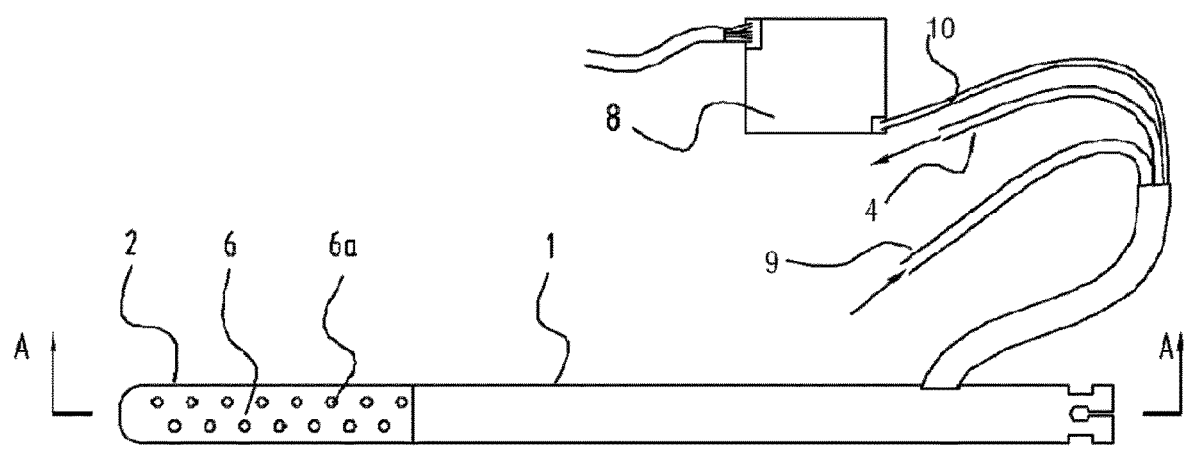
FIG. 1 is a structure diagram of a liquid-collecting mechanism according to the present invention.
Figure 2:
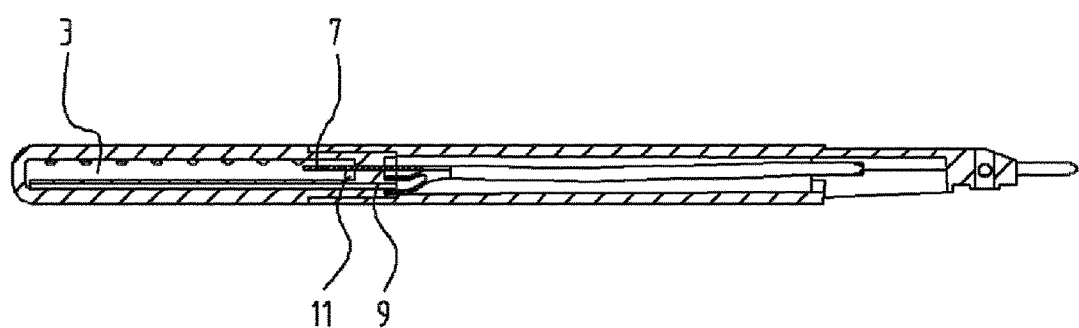
FIG. 2 is a section view of the mechanism shown in FIG. 1 taken along line A-A in FIG. 1.
Figure 3:
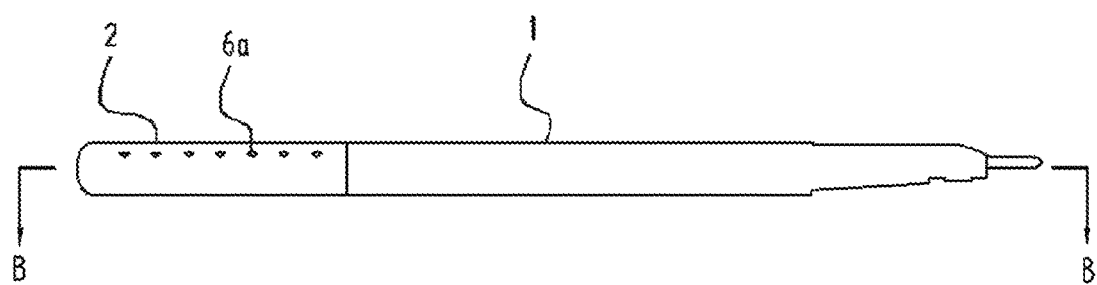
FIG. 3 is a bottom view of a structure of a liquid-collection tube arm in FIG. 1.
Figure 4:
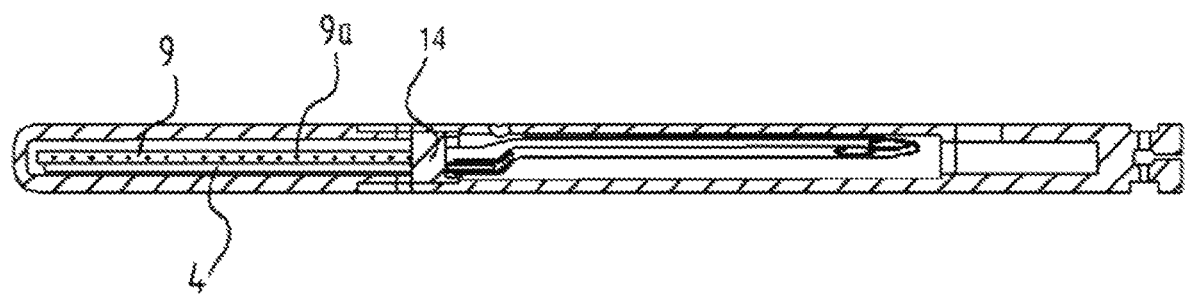
FIG. 4 is a section view of the structure shown in FIG. 3 taken along line B-B in FIG. 3.

FIGS. 1-4 show an embodiment of a liquid collecting mechanism that is configured as a urine-collecting mechanism having a liquid-collection tube arm 1, a liquid-collection tube head 2, a liquid-suction tube 4, and a liquid-discharge tube 9.

The liquid-collection tube arm 1 is shown as a hollow tube fitting, a front end of the liquid-collection tube arm 1 is used for fixing the liquid-collection tube head 2, and a tail end of the liquid-collection tube arm 1 is provided with a tube running groove for leading out the liquid-suction tube 4 and the liquid-discharge tube 9. The liquid-collection tube head 2 is fixed at the front end of the liquid-collection tube arm 1. A sealing spacer 14 is arranged at a joint of the liquid-collection tube head 2 and the liquid-collection tube arm 1. The liquid-collection tube head 2 is internally provided with a liquid-collection cavity 3, where the liquid-collection cavity 3 is enclosed by the inner wall of the liquid-collection tube head 2 and the sealing spacer 14. An area of the liquid-collection tube head 2 located above the liquid-collection cavity 3 is a mesh collection area 6, and the mesh collection area 6 is provided with a plurality of collecting holes 6a. In the illustrated embodiment, the plurality of collecting holes 6a is arranged in an array arrangement mode, so that a larger area for collecting the urine can be obtained. Therefore, the method for moving a position of a urine-suction hole by using a driving mechanism in the prior art is replaced, which reduces the cost. Meanwhile, since the collecting holes 6a have small diameter, blockage caused by external impurities entering into the liquid-collection tube may further be prevented, and the problem of splashing urine may be avoided. It shall be noted that the term "front end" as utilized herein refers to the end of the liquid-collecting mechanism that extends toward a center of a smart toilet employing the mechanism, and the term "rear end" as utilized herein refers to the end of the liquid-collecting mechanism that is configured to be proximate to an edge of the smart toilet.

Openings at one end of the liquid-suction tube 4 and one end of the liquid-discharge tube 9 are located in the liquid-collection cavity 3 (see FIGS. 2 and 4), and the other ends with openings of the liquid-suction tube 4 and the liquid-discharge tube 9 pass through the sealing spacer 14 and the liquid-collection tube arm 1 and are led out from the tube running groove(s), and are used for being connected with a pump body mechanism, such as to suck the urine and discharge the waste under the effect of the pump body mechanism. The liquid-suction tube 4 and the liquid-discharge tube 9 can be formed by a rigid tube or a flexible tube, respectively, or may further be formed by the rigid tube connected with the flexible tube.

In order to prevent the liquid-collection cavity 3 from forming an air trapping area, the liquid-collection tube head 2 is provided with an air discharge hole or groove 11 communicated (e.g., in fluid communication) with the liquid-collection cavity 3. The air discharge hole or the air discharge groove 11 is preferably arranged on one side of the liquid-collection tube head 2 close to the liquid-collection tube arm 1. In this way, when the liquid-collecting mechanism collects the urine, the urine enters into the liquid-collection cavity 3 through the collecting holes 6a of the mesh collection area 6, since the liquid-collecting mechanism is inclined downward by a certain angle, and gas in the liquid-collection cavity 3 can be discharged from the air discharge hole or the air discharge groove 11, thus solving the problem that the liquid-collection cavity 3 cannot be fully filled with the urine.

In the illustrated embodiment, a plurality of auxiliary liquid-discharge holes 9a is provided on a tube wall of the liquid-discharge tube 9 located in the liquid-collection cavity 3. The plurality of auxiliary liquid-discharge holes 9a is axially arranged in an array along the tube wall of the liquid-discharge tube 9. In this way, compared with the prior liquid-discharge tube with only one liquid-discharge port, liquid discharging speed and evacuation rate are greatly improved.

In the illustrated embodiment, the liquid-collection tube head 2, the liquid-collection tube arm 1, and the sealing spacer 14 are integrally formed (e.g., as a unitary member or element), and in this way, when the liquid-collecting mechanism is assembled, the liquid-suction tube 4 and the liquid-discharge tube 9 extend into the liquid-collection cavity 3 through a through hole in the sealing spacer 14. Since the liquid-suction tube 4 and the liquid-discharge tube 9 are both relatively thin, the liquid-suction tube 4 and the liquid-discharge tube 9 are particularly easy to be bent and deformed. To overcome this potential problem, the liquid-suction tube 4 and the liquid-discharge tube 9 can be fixedly connected together in a side by side arrangement, such as through welding or another process, so that the liquid-suction tube 4 and the liquid-discharge tube 9 jointly extend into the liquid-collection cavity 3 through the through hole in the sealing spacer 14. This reduces the difficulty of making the liquid-suction tube 4 and the liquid-discharge tube 9 extend into the liquid-collection cavity 3.

Certainly, the liquid-collection tube head 2, the liquid-collection tube arm 1, and the sealing spacer 14 can be separated (e.g., formed separately then coupled together), according to other embodiments. In this way, the size of the liquid-suction tube 4 and the liquid-discharge tube 9 passing through the sealing spacer 14 may be firstly sized according to a length of the liquid-collection cavity 3. Then, the sealing spacer 14 is installed in the liquid-collection tube arm 1. Finally, the liquid-collection tube head 2 is installed. This design greatly improves accuracy of the length of the liquid-suction tube 4 and the liquid-discharge tube 9 inserting into the liquid-collection cavity 3, and thus improves accuracy of locating the liquid-suction port and the liquid-discharge hole, and improves the evacuation rate of urine sample suction and waste discharge.

The liquid-collection tube arm 1 can be integrated with the sealing spacer 14 to omit the step of assembling the liquid-collection tube arm 1 and the sealing spacer 14 together during the assembly process. Also, the liquid-collection tube head 2 can be integrated with the sealing spacer 14 to omit the step of assembling the liquid-collection tube head 2 with the sealing spacer 14 during the assembly process.

In addition, in the embodiment, the parts of the liquid-suction tube and liquid-discharge tube within the liquid-collection cavity 3 can be integrated with the inner wall of the liquid-collection tube head 2. That is, the said parts of the liquid-suction tube and liquid-discharge tube are directly prepared on (e.g., connected to) the inner wall of the liquid-collection tube head 2 when preparing the liquid-collection tube head 2, thus avoiding a subsequent insertion operation. In this way, the portions of the liquid-suction tube and liquid-discharge tube extending out of the liquid-collection cavity 3 may be respectively connected with the pump body mechanism by a flexible tube.

In the embodiment, the liquid-collecting mechanism can further include a liquid level sensing unit used for monitoring a urine level collected in the liquid-collection cavity 3 in real time, and controlling the start and stop of the pump body mechanism according to the urine level in the liquid-collection cavity 3. The liquid level sensing unit, if provided, includes a steel needle 7, a control circuit board 8, and a wire 10 (e.g., electrical wire). The steel needle 7 can be made of stainless steel (or other suitable material) and serves as an input electrode of the liquid level sensing unit. One end of the steel needle 7 is arranged in the liquid-collection cavity 3, and its end face is located in an upper portion of the liquid-collection cavity 3 and does not exceed a perpendicular plane of the collecting hole 6a closest to the liquid-collection tube arm 1. The other end of the steel needle 7 is electrically connected with the control circuit board 8 through the wire 10.

The detection principle of the liquid level sensing unit is that: when the urine level sucked in the liquid-collection cavity 3 has not yet contacted the end face of the steel needle 7, an input capacitance of the control circuit board 8 is equal to a reference capacitance inside the control circuit plus a capacitance of the steel needle 7 outside the control circuit and a capacitance of the wire 10. Since the capacitance of the steel needle 7 and the capacitance of the wire 10 are very small and negligible, the control circuit board 8 outputs a high level at the moment; when the liquid-collection cavity 3 is full of the urine or the urine contacts the end face of the steel needle 7, an external input capacitance of the control circuit board 8 is equal to the capacitance of urine in the liquid-collection cavity 3 plus the capacitance of the steel needle 7 and the capacitance of the wire 10. Since the capacitance of urine in the liquid-collection cavity 3 is much larger than the capacitances of the steel needle 7 and the wire 10, an input capacitance of the control circuit board 8 is equal to the reference capacitance of the control circuit plus the capacitance of urine in the liquid-collection cavity, and the control circuit board 8 outputs a low level at the moment. And at the moment, the pump body mechanism is controlled to start to suck the urine in the cavity through the liquid-suction tube 4.

For embodiments where the liquid-collection tube head 2, the liquid-collection tube arm 1, and the sealing spacer 14 are separately constructed, the steel needle 7 is firstly inserted into the sealing spacer 14 to determine the length accuracy and verticality of the portion of the steel needle 7 inserting into the liquid-collection cavity 3, which thereby improves the accuracy of the liquid level detection.

According to the present invention, by improving the existing urine-suction hole, the area for collecting the urine can be increased through the array mesh collection area. The improvement of the urine-suction hole can replace the method for moving the position of the urine-suction hole by using a driving mechanism in the prior art, and thereby the cost is reduced, and meanwhile, blockage caused by the external impurities entering into the liquid-collection tube can be prevented, and the problem of splashing urine can be avoided. In addition, a plurality of liquid-discharge holes is distributed in the tube wall of the liquid-discharge tube in the liquid-collection cavity, so that the speed of discharging cleaning liquid can be greatly increased, and the cleaning liquid at each position in the liquid-collection cavity may be discharged.

The foregoing description is merely preferred embodiments of the present invention, but is not intended to limit the present invention in any form, and any simple amendments, equivalent changes or modifications made by those skilled in the art using the technical contents disclosed above shall all fall within the protection scope of the present invention.

What is claimed is:

1. A liquid collecting mechanism, comprising:
   a liquid collection tube arm;
   a liquid collection tube head fixed at a front end of the liquid collection tube arm, wherein the liquid collection tube head is internally provided with a urine collection cavity, an area of the liquid collection tube head located above the urine collection cavity is a mesh collection area, and a plurality of collecting holes is provided in the mesh collection area;
   a sealing spacer arranged at a joint between an end of the liquid collection tube head and an end of the liquid collection tube arm;
   a liquid suction tube passing through a through hole on a surface of the sealing spacer to extend into the liquid collection tube arm, the liquid suction tube comprising:
      a first end having an opening located in the urine collection cavity; and
      a second end having an opening configured to connect with a pump body mechanism; and
   a liquid discharge tube passing through the through hole on a surface of the sealing spacer to extend into the liquid collection tube arm, the liquid discharge tube comprising:
      a first end having an opening located in the urine collection cavity; and a second end having an opening configured to connect with the pump body mechanism;

wherein a tube wall of the liquid discharge tube located in the urine collection cavity includes an auxiliary liquid discharge hole configured to discharge cleaning liquid out of the urine collection cavity.

2. The liquid collecting mechanism of claim 1, wherein the plurality of collecting holes in the mesh collection area is arranged in an array arrangement mode.

3. The liquid collecting mechanism of claim 1, wherein the liquid collection tube head is provided with an air discharge hole or an air discharge groove in fluid communication with the urine collection cavity.

4. The liquid collecting mechanism of claim 1, wherein a plurality of auxiliary liquid discharge holes is arranged in an array along an axial direction of the liquid discharge tube.

5. The liquid collecting mechanism of claim 1, wherein the liquid suction tube and the liquid discharge tube are fixedly connected together in a side by side configuration.

6. The liquid collecting mechanism of claim 1, wherein a portion of the liquid discharge tube located in the urine collection cavity is integrally formed with the liquid collection tube head.

7. The liquid collecting mechanism of claim 6, wherein a portion of the liquid suction tube located in the urine collection cavity is integrally formed with the liquid collection tube head.

8. The liquid collecting mechanism of claim 7, wherein the liquid collection tube head, the liquid collection tube arm, and the sealing spacer are integrally formed as a unitary member.

9. The liquid collecting mechanism of claim 1, wherein at least one of the liquid collection tube head and the liquid collection tube arm is integrally formed with the sealing spacer.

10. The liquid collecting mechanism of claim 1, further comprising a liquid level sensing unit used for monitoring a liquid volume collected in the urine collection cavity in real time.

11. The liquid collecting mechanism of claim 10, wherein the liquid level sensing unit comprises:
a steel needle having a first end arranged in the urine collection cavity and a second end, wherein an end face of the first end of the steel needle is located at an upper portion of the urine collection cavity and does not exceed a vertical plane of a collecting hole of the plurality of collecting holes that is closest to the liquid collection tube arm;
a control circuit board; and
a wire electrically connecting the second end of the steel needle to the control circuit board.

12. A smart toilet, comprising the liquid collecting mechanism of claim 1, wherein when the liquid collecting mechanism collects urine, the urine is received by the plurality of collecting holes in the mesh collection area.

13. A smart toilet having a liquid collecting mechanism, the liquid collecting mechanism comprising:
a liquid collection tube arm;
a liquid collection tube head coupled to an end of the liquid collection tube arm, the liquid collection tube head comprising an outer wall defining a urine collection cavity and having a plurality of collecting holes fluidly connected to the urine collection cavity;
a sealing spacer disposed at a joint between an end of the liquid collection tube head and an end of the liquid collection tube arm;
a liquid suction tube passing through a through hole on a surface of the sealing spacer to extend into the liquid collection tube arm, the liquid suction tube comprising an open first end located in the urine collection cavity and an open second end located outside of the liquid collection tub arm; and
a liquid discharge tube passing through the through hole on a surface of the sealing spacer to extend into the liquid collection tube arm, the liquid discharge tube comprising:
a first end having an opening located in the liquid collection urine cavity; and
a second end having an opening;
wherein a tube wall of the liquid discharge tube located in the liquid collection urine cavity includes an auxiliary liquid discharge hole configured to discharge cleaning liquid out of the urine collection cavity.

14. The smart toilet of claim 13, further comprising a pump body mechanism, wherein the open second end of the liquid suction tube is configured to connect with the pump body mechanism.

15. The smart toilet of claim 14, further comprising a liquid level sensing unit configured to monitor a liquid volume collected in the urine collection cavity in real time.

16. The smart toilet of claim 15, wherein the liquid level sensing unit comprises a needle having a first end located in the urine collection cavity and a second end, a control circuit board, and a wire electrically connecting the second end of the needle to the control circuit board.

17. The smart toilet of claim 16, wherein an end face of the first end of the needle is located at an upper portion of the urine collection cavity and does not exceed a vertical plane of a collecting hole of the plurality of collecting holes that is closest to the liquid collection tube arm.

18. The smart toilet of claim 17, wherein the opening of the second end is configured to connect with the pump body mechanism.

19. A liquid collecting mechanism, comprising:
a liquid collection tube arm;
a liquid collection tube head fixed at a front end of the liquid collection tube arm, wherein the liquid collection tube head is internally provided with a urine collection cavity;
a sealing spacer arranged at a joint between an end of the liquid collection tube head and an end of the liquid collection tube arm;
a liquid suction tube passing through a through hole on a surface of the sealing spacer to extend into the liquid collection tube arm; and
a liquid discharge tube passing through the through hole on a surface of the sealing spacer to extend into the liquid collection tube arm,
wherein a tube wall of the liquid discharge tube located in the urine collection cavity includes an auxiliary liquid discharge hole configured to discharge cleaning liquid out of the urine collection cavity.

20. The liquid collecting mechanism according to claim 19, wherein an area of the liquid collection tube head located above the urine collection cavity is a mesh collection area,
wherein a plurality of collecting holes is provided in the mesh collection area,
wherein the liquid suction tube comprises:
a first end having an opening located in the urine collection cavity; and
a second end having an opening configured to connect with a pump body mechanism, wherein the liquid discharge tube comprises:
- a first end having an opening located in the urine collection cavity; and
- a second end having an opening configured to connect with the pump body mechanism.

* * * * *